(12) United States Patent
Kalvesten et al.

(10) Patent No.: US 8,880,143 B2
(45) Date of Patent: Nov. 4, 2014

(54) APPARATUS AND METHOD FOR ESTIMATING THE BONE MINERAL DENSITY TO ASSES BONE FRACTURES RISK

(75) Inventors: Johan Kalvesten, Linkoping (SE); Jakob Algulin, Linkoping (SE)

(73) Assignee: Sectra Imtec AB, Linkoping (SE)

( * ) Notice: Subject to any disclaimer, the term of this patent is extended or adjusted under 35 U.S.C. 154(b) by 346 days.

(21) Appl. No.: 13/351,792

(22) Filed: Jan. 17, 2012

(65) Prior Publication Data
US 2013/0184556 A1 Jul. 18, 2013

(51) Int. Cl.
*A61B 6/00* (2006.01)
*G06T 7/00* (2006.01)
*A61B 5/00* (2006.01)

(52) U.S. Cl.
CPC ..... *G06T 7/0014* (2013.01); *G06T 2207/10116* (2013.01); *A61B 6/505* (2013.01); *A61B 5/4509* (2013.01); *G06T 2207/30008* (2013.01)
USPC .............. 600/407; 382/132; 378/54

(58) Field of Classification Search
USPC .............. 600/407; 382/132; 378/54
See application file for complete search history.

(56) References Cited

U.S. PATENT DOCUMENTS

| | | | |
|---|---|---|---|
| 5,852,647 A * | 12/1998 | Schick et al. | 378/53 |
| 6,763,257 B1 * | 7/2004 | Rosholm et al. | 600/407 |
| 2003/0198316 A1 * | 10/2003 | Dewaele et al. | 378/54 |

* cited by examiner

*Primary Examiner* — Jonathan Cwern
(74) *Attorney, Agent, or Firm* — Pearl Cohen Zedek Latzer Baratz LLP

(57) ABSTRACT

The present invention relates to a method for estimating the Bone Mineral Density (BMD) using image data collected in emergency situation, i.e. without following specific protocols. In particular, the invention discloses a method for assessing the risk of bone fractures using as one indicator a BMD of one or more bones. The BMD is calculated using a universal constant which provides a value of BMD having a certain error in respect to its true value. However this error does not substantially affect the assessment of the risk of fracture of one or more bones.

6 Claims, 2 Drawing Sheets

APPARATUS AND METHOD FOR ESTIMATING THE BONE MINERAL DENSITY TO ASSES BONE FRACTURES RISK

FIELD OF THE INVENTION

The present invention relates to a method for estimating the Bone Mineral Density using a radiogrammetry. The present invention also relates to a method for assessing the risk of bone fractures using indicators such as the BMD of one or more bones.

BACKGROUND OF THE INVENTION

Osteoporosis is a disease of bones that leads to an increased risk of bones fracture. Generally, osteoporosis implies a reduction of bone mineral density (BMD) and may lead to pathologic or fragility fractures. Previous fragility fractures indicate that there is a strong risk for future fragility fractures. In that an estimate of BMD and an assessment of the fracture risk may be crucial to prevent future bones fractures.

Bones are formed by two types of osseous tissue, i.e. compact tissue or cortical bone tissue and cancellous bone tissue.

Bone Mineral Density (BMD) is often determined by Radiogrammetry image processing of an x-ray image (DXR-BMD). Among the techniques used for measuring BMD, the determination of BMD based on digital x-ray radiogrammetry, resides in the evaluation of the thickness of the cortical bone tissue and the width of the bone of interest. Determining these parameters, from, for example, a digitized X-ray image acquired with the maximum resolution offered by today's standard medical X-ray machines is a difficult task.

U.S. Pat. No. 6,763,257 discloses a method for estimating BMD by the use of radiogrammetry. The BMD is calculated based on a functional relationship between thickness (T) of the cortical bone tissue and the width (W) of the bone of interest, according to a function having the following appearance:

$$BMD = B \times T \times (1 - T/W)$$

where B is determined from a calibration where pairs of (T, W) have been calibrated to corresponding BMD values for one or more bones.

Generally, this calibration may include the calibration for each type of image sources, e.g. for different model and types of X-ray detector system and different acquisition modalities. This calibration generates a B which can be used in the estimate of BMD based on image data collected through a specific protocol, e.g., exposure setting, such as focus distance, energy used, and post processing, such as edge enhancement.

However, in several situations, such as emergency situations, the specific protocol for acquiring radiograms cannot be followed, hampering the usability of DXR for the estimate of BMD.

Hence, an improved method for estimating BMD of a bone would be advantageous, and in particular a more efficient and/or reliable method for assessing the risk of bone fractures from image data collected in emergency situation would be advantageous.

OBJECTS OF THE INVENTION

One, some of all of the below objects may be partially or fully realized by various embodiments of the invention. It is an object of the invention to provide a method for estimating BMD. It is a further object of the invention to provide a method for assessing the risk of bone fractures. It is an even further object of the present invention to provide an alternative to the prior art. In particular, it may be seen as an object of the present invention to provide a method for assessing the risk of bone fractures that solves the above mentioned problems of the prior art by assessing the risk of bone fractures from image data collected in emergency situation. It will be understood that some embodiments of the invention need not satisfy various of the above objects.

SUMMARY OF EMBODIMENTS OF THE INVENTION

The present invention relates to a method for estimating the Bone Mineral Density (BMD) using image data collected in emergency situation, e.g., without following specific protocols. In particular, embodiments of the invention discloses an apparatus and method for assessing the risk of bone fractures using as one indicator a BMD of one or more bones. The BMD may be calculated using a universal constant which provides a value of BMD having a certain error in respect to its true value. However, this error does not substantially affect the assessment of the risk of fracture of one or more bones.

BRIEF DESCRIPTION OF THE FIGURES

The method according to the invention will now be described in more detail with regard to the accompanying figures. The figures show one way of implementing the present invention and is not to be construed as being limiting to other possible embodiments falling within the scope of the attached claim set.

Figure 1:
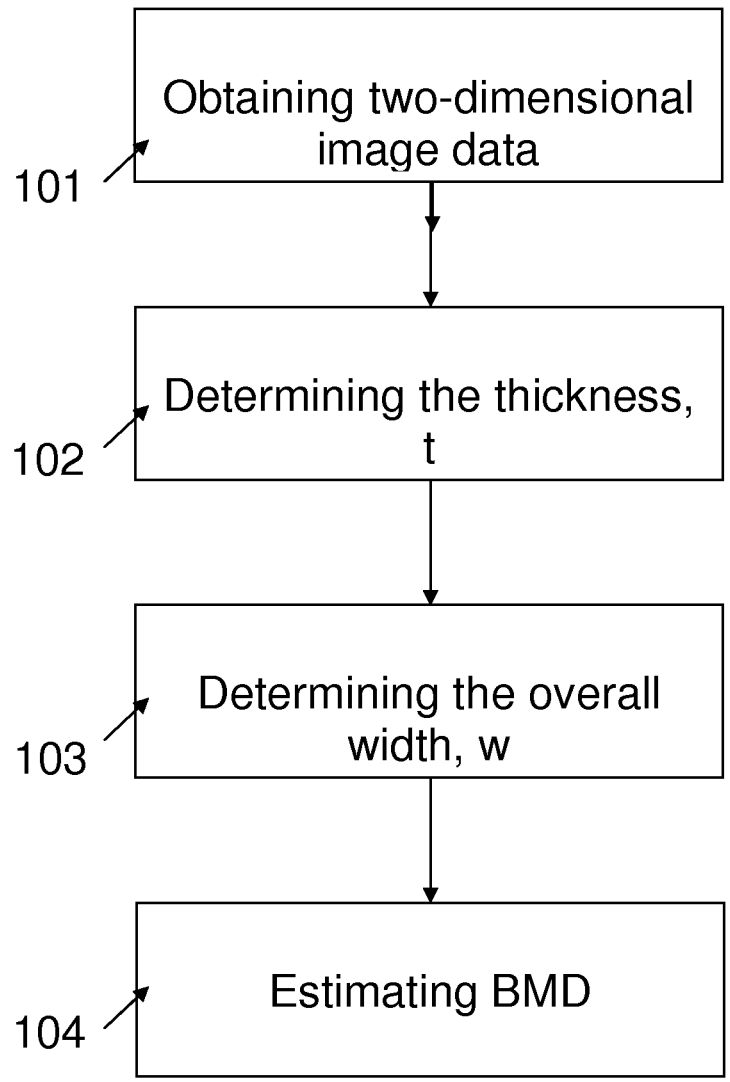
FIG. 1 is a flow-chart of a method for estimating the BMD of a bone according to the invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF EMBODIMENTS OF THE INVENTION

Unless specifically stated otherwise, as apparent from the following discussions, it is appreciated that throughout the specification discussions utilizing terms such as "processing," "computing," "calculating," "determining," "estimating" or the like, may refer to the action and/or processes of a computer, computer processor, computing system, computer network, or similar electronic computing device, that manipulates and/or transforms data represented as physical, such as electronic, quantities within the computing system's registers and/or memories into other data similarly represented as physical quantities within the computing system's memories, registers or other such information storage, transmission or display devices. In some embodiments of the invention, various parameters may be obtained by a calculation process by the computing device, or they may be manually entered by a user so as to allow the computing device to perform calculations based thereupon.

Embodiments of the present invention may include an apparatus for performing the methods and operation described herein. Such an apparatus according to embodiments of the invention may be specially constructed for the desired purposes, or it may comprise a general-purpose computer selectively activated, configured, instructed, or programmed by a computer program stored in a non-transitory computer memory. Such a computer program may be stored, in a manner so as to be accessible locally or remotely, in a computer readable storage medium, such as, but not limited to, any type of disk, including floppy disks, optical disks, magnetic-optical disks, read-only memories (ROM's), compact disc read-only memories (CD-ROM's), random access memories (RAM's), electrically programmable read-only memories (EPROM's), electrically erasable and programmable read only memories (EEPROM's), FLASH memory, magnetic or optical cards, or any other type of media suitable for storing electronic instructions and capable of being coupled to a computer system bus.

The methods presented herein need not be inherently related to any particular computer or other apparatus. Various general-purpose systems may be used with programs in accordance with the teachings herein, or it may prove convenient to construct a more specialized apparatus to perform the desired method. The desired structure for a variety of these systems will appear from the description below. It will be appreciated that a variety of programming languages may be used to implement the teachings of embodiments of the invention as described herein.

It should be appreciated that according to some embodiments of the present invention, the method described below, may be implemented in machine-executable instructions. These instructions may be used to cause a general-purpose or special-purpose processor that is programmed with the instructions to perform the operations described. Alternatively, the operations may be performed by specific hardware that may contain hardwired logic for performing the operations, or by any combination of programmed computer components and custom hardware components.

The method may be provided as a computer program product that may include a machine-readable medium having stored thereon instructions that may be used to program a computer (or other electronic device) to perform the method. For the purposes of this specification, the terms "machine-readable medium" may include any medium that is capable of storing or encoding a sequence of instructions for execution by the machine and that cause the machine to perform any one of the methodologies of the present invention. The term "machine-readable medium" may accordingly include, but need not be limited to, solid-state memories, optical and magnetic disks, and a carrier wave that encodes a data signal.

Although the scope of the present invention is not limited in this respect, the system and method disclosed herein may be implemented in many wireless, handheld and portable communication devices. By way of example, wireless, handheld and portable communication devices may include wireless and cellular telephones, smart telephones, personal digital assistants (PDAs), web-tablets and any device that may provide wireless access to a data network such, an intranet or the Internet. It should be understood that the present invention may be used in a variety of applications.

Objects of the invention may be obtained in a first aspect of the invention by providing an apparatus and method for estimating the Bone Mineral Density (BMD) of a bone, the method comprising: obtaining two-dimensional image data comprising information relating to the cortical bone tissue of a first bone or at least a part of said first bone, the image data being data acquired by exposing at least part of said first bone to electromagnetic radiation, determining a thickness, t, of the cortical bone tissue of said first bone, determining an overall width, w, of said first bone, estimating the BMD of said first bone as:

$$BMD = A \times t(1-t/w), \qquad (\text{eq. 1})$$

wherein A is determined by correlating pair of t and w to corresponding BMD values for one or more bones and wherein A is used for the estimate of BMD independently from the modalities of acquisition of the two-dimensional image data. Thereby a BMD value having an error, in percent, in respect to the true value of BMD up to 10% is produced. The meaning of independently will be readily understood based on the discussion hereinbelow.

Constant A can be used in the estimate of the BMD according to the equation above when t and w values have been determined from two-dimensional image data that have been acquired without following a specific protocol, i.e. a specific modalities of image acquisition. Independent therefore defines that the use of constant A in the equation for calculation of the BMD does not depend or is not linked neither to the way or modalities in which the two-dimensional image have been acquired nor to the way or modalities in which the two-dimensional image data have been acquired and or extracted from those two-dimensional images.

Independent as defined in the invention is therefore to be interpreted as independent from the acquisition modalities of the two-dimensional image data as these modalities will not influence the way the constant A is originated. Thus constant A is estimated so as to be independent from the image acquisition modalities of the two-dimensional image data used for providing an estimate of the BMD.

Correlating may be also interpreted as connecting or creating a relationship between the pair of t and w and the BMD values.

This method allows for the calculation of the BMD on the X-ray image used to assess the fracture or repositioning of the fracture, e.g. acquired in an emergency room. An advantage of the method of the invention is therefore that there is no need to follow a specific acquisition protocol as the constant A used for estimating the BMD is a universal constant which provides a value of BMD within a certain error which does not affect the assessment of the risk of fracture of one or more bones.

Indeed, the estimate of the BMD according to the first aspect of the invention, i.e., by using a constant A which is independent from the modality in which the two-dimensional image data have been acquired, introduces an error in the estimate of the BMD in respect to its true value.

The BMD obtained using the method, because of this error, cannot always be used, e.g., cannot be used in the identification of BMD change rate.

However, surprisingly, it has been found by the inventors through statistical analysis of several data that a reduced precision by few percent achieved in the estimate of the value of BMD according to the method does not significantly reduce the quality of the fracture risk prediction performance of DXR-BMD. Thus BMD values estimated through the method of the invention, despite the error in respect to the true value of BMD, when employed in the fracture risk prediction, surprisingly provide a correct prediction of the risk of bones fracture. Thus, const A is used to estimate BMD independently from said two-dimensional image data acquisition modalities.

By using constant A the method according to the first aspect of the invention has the advantage that the BMD estimated value can be used to evaluate the bone fragility also in emergency situation solving the problem of the prior art.

The constant A is determined by correlating pair of t and w to corresponding BMD values for one or more bones. Several values of t and w of several bones are correlated to corresponding BMD values obtained through other methods. In this way a general correlation between values of t and w and values of BMD can be obtained. No influence from the acquisition modalities into the estimate of the BMD is considered. This leads to a constant A having an error, which is relative low, e.g. less than 10%, and which does not significantly reduce the fracture risk prediction performance of DXR-BMD. The reason for this resides in the way the fracture risk assessment is calculated as described below.

Fracture risk assessment is estimated by combining: a) person information, such as age, gender, weight and height; b) clinical risk factors, such as frequency of previous fractures, diseases, e.g. Rheumatoid arthritis, alcohol consumption, smoking habits; c) number of standard deviations below the average for a young adult at peak bone density, i.e. T-scores or Z-scores.

T-scores values are obtained from BMD values following converting equations, for example:

$$T-\text{score} = \frac{(BMD - BMD_{ref})}{SD}, \quad \text{(eq. 2)}$$

Wherein $BMD_{ref}$ is the average BMD of a young healthy reference population and SD is the standard deviation of BMD in the reference population. The $BMD_{ref}$ generally depends on the bone density but also on ethnicity, gender and location in the skeleton. Therefore introducing an error having a low magnitude causes only a relative small reduction in the standard deviation, i.e. the relative risk. For example an error in BMD lower than 10% generate an error in T-score of ca 1 unit, i.e. within a value which does not substantially affect the estimate of the risk of bone fracture.

Constant A may be determined through the analysis of previous two-dimensional image data.

Previous is herein defined as previously analyzed or previously recorded, however not referred to the same first bone, e.g. previously analyzed or previously recorded two-dimensional image data of a second bone that may be a different bone of the same person of the first bone, or which may be the same kind of bone or a different bone of other people.

The previous two-dimensional image data may comprise information relating to a second or more bones or at least part of said second or more bones. This second bone may not belong to the same person of the first bone.

Constant A may be determined employing values of parameters not originated from the two-dimensional image data.

In general, constant A is not determined from a calibration where pairs of t and w have been calibrated to corresponding BMD values for one or more bones.

Preferably, constant A does not depend on any other measure derived from the two-dimensional image data comprising information relating to the first bone or at least part of the first bone.

In some embodiments constant A is a function of calibrated constants. In that constant A is determined based on a number of calibrated constants.

Function is herein defined as referred to any mathematical operation producing constant A value from one or more calibrated constants input values.

In some embodiments constant A is an average of calibrated constants.

Average is defined herein as the central tendency of a data set, e.g. arithmetic, geometric or harmonic mean.

In some other embodiments constant A is a weighted average of calibrated constants.

The weighted average of calibrated constants may be weighted to optimize specific functions in some embodiments.

At least one of the specific functions may be the total expected error for all calibrated image sources in some embodiments.

Optimize a function is referred herein as mathematical optimization such as maximizing or minimizing a mathematical function.

In some embodiments at least one of the specific functions may be the maximum error of calibrated constant for any image source, e.g. the average of the highest and lowest of any applicable calibrated constants.

In some further embodiments the calibrated constants are constants determined from a calibration where pairs of t and w have been calibrated to corresponding BMD values for one or more bones determined from previous two-dimensional image data. Previous two-dimensional image data are not the two-dimensional image data obtained by exposing at least part of the first bone to electromagnetic radiation. Previous two-dimensional image data may be the image data obtained by exposing at least part of one or more bones, other than the first one, to electromagnetic radiation.

For example BMD of a first bone of a person, such as a femur, may be estimated using a A that is a function of calibrated constant determined from a calibration where pairs of t and w have been calibrated to corresponding BMD values for one or more bones, such as femurs determined from previous two dimensional image data of femurs of other people.

The calibrated constants may be determined from a calibration where pairs of t and w have been calibrated to corresponding BMD values for one or more second bones. For one or more second bones is intended bones which are not the first bone or at least part of the first bone.

For example, BMD of a first bone of a person, such as a femur, may be estimated using a constant A that is a function of calibrated constant determined from a calibration where pairs of t and w have been calibrated to corresponding BMD values for one or more bones, such as phalanges or metacarpals determined from previous two dimensional image data of phalanges or metacarpals of the same person or other people. The calibrated constants, herein referred to, may be constants determined from a calibration derived from previous two-dimensional image data that are not the two-dimensional image data obtained by exposing at least part of the first bone to electromagnetic radiation.

In some embodiments the calibrated constants are calibrated to combinations of pairs of t and w determined from previous two-dimensional image data collected in different image acquisition modalities.

In some embodiments the method according to the first aspect of the invention comprises: determining a direction at least substantially perpendicular to a longitudinal axis of the bone; determining a thickness, t, of the cortical bone tissue of the first bone along that direction; determining an overall width, w, of the first bone along that direction.

Values of t and w may be determined along a single line extending in that direction. Pairs of t and w may be determined for a plurality of individual lines extending in the direction and being positioned at different positions along the longitudinal direction of the bone, and wherein the BMD is determined on the basis of pairs of t and w corresponding to the individual lines.

The BMD may be determined on the basis of mean values of the t and w values corresponding to the individual lines.

In some embodiments the first or second bone is a tubular bone, such as a bone chosen from the group consisting of radius, ulna, tibia, fibula, metacarpal, phalanges and femur. In some other embodiments the first or second bone is a radius, and the t value or values is/are determined on a radial side of the radius. In some further embodiments the first or second bone is an ulna, and the t value or values is/are determined on an ulnar side of the ulna.

According to a second aspect of the invention a method for estimating a bone fracture risk is provided employing as an indicator a BMD value having an error, in percent, in respect to the true value of BMD up to 10%.

In some embodiments the error is a Gaussian error.

In some further embodiments the error in respect to the true value of BMD is between 1 and 10%, such as between 2 and 10%, such as between 5 and 10%.

According to the second aspect of the invention in the method for estimating a bone fracture risk, the BMD is estimated through the method for estimating the BMD of a bone according to the first aspect of the invention.

In a third aspect a method for estimating a bone fracture risk is provided employing as an indicator BMD estimated according to the method for estimating the BMD of a bone according to the first aspect of the invention.

In some embodiments the method for estimating a bone fracture risk according to the second aspect of the invention comprises: estimating the BMD of a bone according to the first aspect of the invention; converting the BMD into a T-score value; evaluating clinical risk factors; calculating the probability of risk of fracture by combining T-score values and clinical risk factors.

Examples of person information are age, gender, weight and height. Clinical risk may be frequency of previous fractures, diseases, e.g. Rheumatoid arthritis, or alcohol consumption, smoking habits.

In some embodiments Z-score can be used instead of T-score.

T and Z-scores are based on the statistical unit of the standard deviation.

The T-score is the number of standard deviations below the average for a young adult at peak bone density. There are different T-scores depending on which group of young adults was used as the reference, e.g., Caucasian women or Hispanic men. The T-score does not necessarily have to compare people of the same ethnicity or gender.

T-scores values may be obtained from BMD values following converting equations, such as equation 2.

The Z-score is the number of standard deviations below an average person of the same age. There are also different Z-scores depending on the group used as a reference, e.g. the group could include everybody of the same age, or it could be limited to people with the same age, ethnicity, gender and weight.

Z-scores can be used to compare a measurement to a reference value. The Z-score is the number of standard deviations away from the average value of the reference group. This reference group usually consists of people of the same age and gender; sometimes ethnicity and weight are also included. A person who is average has a Z-score of zero.

Using statistical models on BMD and bones fractures frequency in a large population, the risk of fracture for each standard deviation below the mean for the age, ethnicity and gender may be calculated. These risks depend on the population, skeletal site of measurement, technique of measurement, and type of fracture.

In a fourth aspect of the invention a method for estimating a bone fracture risk is provided, the method comprising: estimating the BMD of a bone according to the first aspect of the invention; converting the BMD into a T-score value; evaluating clinical risk factors; calculating the probability of risk of fracture by combining T-score values and clinical risk factors.

The above first, second, third, and fourth aspects of the present invention may each be combined with any of the other aspects of the invention. These and other aspects of the invention will be apparent from and elucidated with reference to the embodiments described herein.

FIG. 1 shows a flow-chart of a method for estimating the BMD of a bone according to the invention.

The method for estimating the BMD of a bone comprises four steps S1-S4. The first step 101 comprises obtaining two-dimensional image data. The two-dimensional image data comprise information relating to a first bone or at least a part of the first bone and are acquired by exposing at least part of the first bone to electromagnetic radiations, e.g. X-rays. From the two-dimensional image data in step 102, the thickness, t, and in step 103 the overall width, w, of the first bone is determined. In step 104 the BMD of the first bone is estimated according to equation 1, wherein A is determined by correlating pair of t and w to corresponding BMD values for one or more bones and wherein A is used for the estimate of BMD independently from the modalities of acquisition of the two-dimensional image data.

Figure 2:
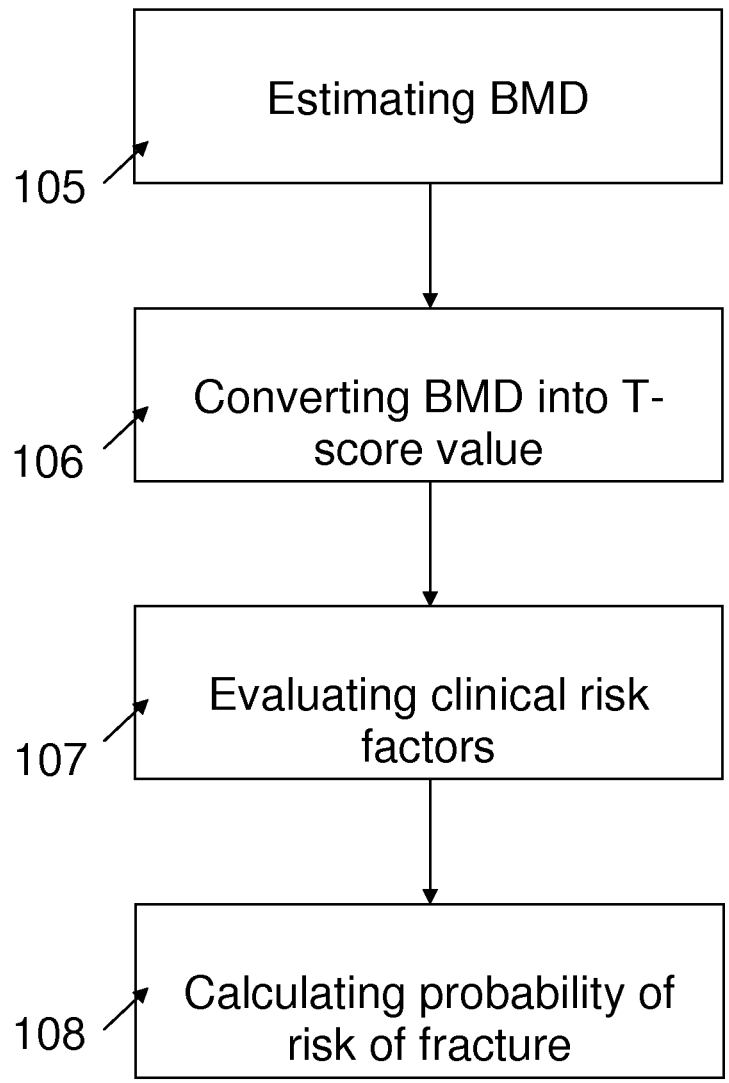
FIG. 2 is a flow-chart of a method for estimating the risk of a bone fracture according to the invention.

FIG. 2 shows a flow-chart of a method for estimating the risk of a bone fracture according to the invention.

The method estimating a bone fracture risk comprises four steps S5-S8. In the first step 105 the BMD of a bone is estimated according to the first aspect of the invention. In the second step 106 the BMD is converted into a T-score value. The BMD value calculated according to equation 1 in step 105 is converted into T-score value according to equation 2 in step 106.

Clinical risk factors are evaluated in step 107.

For example to evaluate clinical risk factors a questionnaire may be completed by a person with questions including the risk factors: age, sex, weight (kg), height (cm), previous fracture, parent fractured hip, smoking and alcohol habits, Glucocorticoids history and bone diseases.

A previous fracture refers to a previous fracture in adult life occurring spontaneously, or a fracture arising from trauma which, in a healthy individual, would not have resulted in a fracture, e.g. a fragility fracture.

The parent fracture hip may provide information regarding the history of hip fracture in the person's mother or father.

Glucocorticoids history may provide information if the person is currently exposed to oral glucocorticoids or has been exposed to oral glucocorticoids for more than 3 months.

Bone diseases may be Rheumatoid arthritis, secondary osteoporosis or disorders associated with osteoporosis. These include type I (insulin dependent) diabetes, osteogenesis imperfecta in adults, untreated long-standing hyperthyroidism, hypogonadism or premature menopause (<45 years), chronic malnutrition, or malabsorption and chronic liver disease.

Finally, in step 108 the probability of risk of fracture is calculated by combining T-score values and clinical risk factors.

Although the present invention has been described in connection with the specified embodiments, it should not be construed as being in any way limited to the presented examples. The scope of the present invention is set out by the accompanying claim set. In the context of the claims, the terms "comprising" or "comprises" do not exclude other possible elements or steps. Also, the mentioning of references such as "a" or "an" etc. should not be construed as excluding a plurality. The use of reference signs in the claims with respect to elements indicated in the figures shall also not be construed as limiting the scope of the invention. Furthermore, individual features mentioned in different claims, may possibly be advantageously combined, and the mentioning of these features in different claims does not exclude that a combination of features is not possible and advantageous.

The invention claimed is:

1. A method for estimating a bone fracture risk for a person, the method employing as an indicator a BMD value having an error with respect to a true value of BMD of up to 10%, the method comprising:
   estimating the Bone Mineral Density (BMD) of a bone of a person, said estimating comprising:
      obtaining two-dimensional image data comprising information relating to the cortical bone tissue of at least a part of a first bone of said person, the image data being data acquired by exposing at least part of said first bone of said person to electromagnetic radiation;
      determining a thickness, t, of the cortical bone tissue of said first bone of said person;
      determining an overall width, w, of said first bone of said person; and
      estimating the BMD of said first bone of said person as: BMD=A×t(1−t/w), wherein A is an average of calibrated constants and wherein said calibrated constants are constants determined from a calibration where pairs of t and w have been calibrated to corresponding BMD values for one or more bones of said person or for said first bone or one or more bones of other people determined from previous two-dimensional image data and wherein A is used for the estimate of BMD independently from the modalities of acquisition of said previous two-dimensional image data;
   converting the BMD into a T-score value;
   evaluating clinical risk factors; and
   calculating the probability of risk of fracture based on the T-score values and the clinical risk factors.

2. The method according to claim 1, wherein A is a weighted average of calibrated constants.

3. The method according to claim 2, wherein said weighted average of calibrated constants is weighted to optimize specific functions.

4. The method according to claim 1, wherein said calibrated constants are determined from a calibration where pairs of t and w have been calibrated to corresponding BMD values for one or more second bones of said person.

5. The method according to claim 1, wherein said calibrated constants are calibrated to combinations of pairs of t and w determined from previous two-dimensional image data collected using different image acquisition modalities.

6. A non-transitory computer-readable medium having instructions stored thereon, wherein said instructions when executed by a processor, cause the processor to:
   obtain two-dimensional image data comprising information relating to the cortical bone tissue of at least a part of a first bone, the image data being data acquired by exposing at least part of said first bone to electromagnetic radiation;
   determine a thickness, t, of the cortical bone tissue of said first bone;
   determine an overall width, w, of said first bone; and
   estimate the BMD of said first bone as: BMD=A×t(1−t/w), wherein A is an average of calibrated constants and wherein said calibrated constants are constants determined from a calibration where pairs of t and w have been calibrated to corresponding BMD values for one or more bones of said person or for said first bone or one or more bones of other people determined from previous two-dimensional image data;
   and wherein A is used for the estimate of BMD independently from the modalities of acquisition of said previous two-dimensional image data and wherein said BMD has an error with respect to a true value of BMD of up to 10%;
   converting the BMD into a T-score value;
   evaluating clinical risk factors; and
   calculating the probability of risk of fracture based on the T-score values and the clinical risk factors.

* * * * *